(12) United States Patent
Sharma

(10) Patent No.: US 10,660,976 B2
(45) Date of Patent: May 26, 2020

(54) COMPOSITIONS AND METHODS FOR AL AMYLOID DETECTION AND USES THEREOF

(71) Applicant: Vijay Sharma, St. Louis, MO (US)

(72) Inventor: Vijay Sharma, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/181,628

(22) Filed: Nov. 6, 2018

(65) Prior Publication Data

US 2019/0134233 A1 May 9, 2019

Related U.S. Application Data

(60) Provisional application No. 62/581,973, filed on Nov. 6, 2017.

(51) Int. Cl.
| | | |
|---|---|---|
| *A61K 51/00* | (2006.01) | |
| *A61M 36/14* | (2006.01) | |
| *A61K 51/04* | (2006.01) | |
| *G01N 33/68* | (2006.01) | |
| *G01N 33/58* | (2006.01) | |
| *G01N 33/60* | (2006.01) | |
| *A61K 51/12* | (2006.01) | |

(52) U.S. Cl.
CPC .......... *A61K 51/04* (2013.01); *A61K 51/0455* (2013.01); *A61K 51/1244* (2013.01); *G01N 33/587* (2013.01); *G01N 33/60* (2013.01); *G01N 33/6896* (2013.01); *G01N 2333/4709* (2013.01); *G01N 2800/52* (2013.01); *G01N 2800/56* (2013.01)

(58) Field of Classification Search
CPC .............. A61K 51/04; A61K 51/1244; G01N 33/6896; G01N 33/587; G01N 33/60; G01N 2333/4709; G01N 2800/52
USPC ...................................................... 424/1.65
See application file for complete search history.

(56) References Cited

FOREIGN PATENT DOCUMENTS

WO WO-2015051188 A1 * 4/2015 ........... C07D 417/06

OTHER PUBLICATIONS

Ehrnhoefer et al. Nat. Struct. Mol. Biol. 2008, 559-566.*
Dorbala et al. Eur. J. Nucl. Med. Imaging 2014, 1652-1662.*
Kyle et al. Clin. Lymph. Myel. 2009, 278-288.*
Jia et al. Dalton Trans. 2015, 44, 6406-6415.*
Matsumura et al. Bioorg. Med. Chem. 2013, 3356-3362.*
Shenoy et al. Int. J. Nanomed. 2006, 51-57.*

* cited by examiner

*Primary Examiner* — Michael G. Hartley
*Assistant Examiner* — Sean R Donohue

(57) ABSTRACT

Among the various aspects of the present disclosure is the provision of compositions and methods for imaging and treating subjects with amyloidosis or multiple myeloma with or without amyloidosis.

18 Claims, 5 Drawing Sheets

COMPOSITIONS AND METHODS FOR AL AMYLOID DETECTION AND USES THEREOF

CROSS-REFERENCE TO RELATED APPLICATIONS

This application claims priority from U.S. Provisional Application Ser. No. 62/581,973 filed on 6 Nov. 2017, which is incorporated herein by reference in its entirety.

STATEMENT REGARDING FEDERALLY SPONSORED RESEARCH OR DEVELOPMENT

This invention was made with government support under grant numbers AG050263 and HL111163 awarded by National Institutes of Health. The government has certain rights in the invention.

MATERIAL INCORPORATED-BY-REFERENCE

Not applicable.

FIELD OF THE INVENTION

The present disclosure generally relates to new compositions of matter and their uses in imaging and therapy.

BACKGROUND OF THE INVENTION

Multiple myeloma (MM) is the second most common hematologic malignancy after non-Hodgkin's lymphoma, with an estimated 20,520 patients diagnosed with the disease and an estimated 10,610 deaths from MM in the U.S. in 2011.[5,6] In 2016, there were an estimated 30,330 newly diagnosed cases in US, therefore accounting for ~1.8% of all new cancer cases.[7] The estimated prevalence of MM in U.S. is 65,000 patients.[5] The incidence of MM increases with age, with the median age at diagnosis being 69 years.[5] The most common signs and symptoms of MM include hypercalcemia, renal dysfunction, anemia, and bone lesions, the CRAB criteria[8,9]. Bone pain is often an initial symptom of the disease.[10] Symptoms often require specific management in addition to direct anti-MM treatment strategies. FDA approved targeted agents, such as the proteasome inhibitor bortezomib (BOR), and thalidomide and lenalidomide, the immunomodulatory agents (IMiDs) have shown remarkable improvements in MM patients.[11-13] While bortezomib (Velcade; Janssen-Cilag, Neuss, Germany) is a well-established therapeutic option in systemic light chain (AL) amyloidosis, the combination therapy involving cyclophosphamide, bortezomib, and dexamethasone (CyBorD) has shown promising effects in MM patients.[14-16] Recent clinical studies in a cohort of 70 MM patients show higher concentration of κ and λ soluble free LC (sFLCs) than their counterparts without amyloidosis, while also indicating highest concentration of κ and λ sFLCs in the group of patients with amyloidosis and renal failure.[17] These data indicate that sFLCs concentrations could be employed as critical biomarker for differentiation of MM patients with or without amyloidosis and provide guidelines for stratification of a pool of patients susceptible to a risk factor for renal failure.

Importantly, although both AL amyloidosis and MM are caused by clonal plasma cells, the two disorders present surprisingly different phenotypes. AL amyloidosis leads to deposits of amyloid protein aggregates in various organs (e.g., kidney, heart, liver, spleen, peripheral nerves, GI tract) resulting in impairment of their normal function. Within symptomatic MM patients, accumulation of clonal plasma cells and monoclonal immunoglobin proteins mediated by hypercalcemia, renal insufficiency, anemia and osteolytic bone lesions (CRAB criteria) results in the organ failure.[18] While amyloid plaques are ascertained via histochemical staining of biopsied specimens using Congo red; MM patients have been shown to be amyloid positive yet Congo red negative. The lack of a clear biochemical distinction between MM and AL mandates discovery and development of ultrasensitive and specific agents for detecting AL amyloidosis in vitro and in vivo. Given that direct confirmation of AL amyloidosis through laser-driven micro-dissection and mass spectrometry analysis is confined to a few facilities nationwide, ultrasensitive diagnostic noninvasive agents capable of detecting AL amyloidosis are urgently mandated. These agents could allow stratification of MM patients for therapeutic interventions and monitor efficacy of therapeutics. This stratification continues to be the most desirable yet an unmet goal in the management of MM.

SUMMARY OF THE INVENTION

Among the various aspects of the present disclosure is the provision of compositions and methods for imaging and treating amyloidosis.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 5B. LC monomers (M)

and dimers (D) detected by coomassie staining after SDS-PAGE under reducing (r) and non-reducing (nr) conditions. Of note is the high purity (>90%) of LC isolated from pre-proteinuric patients.

Figures 6A, 6B:
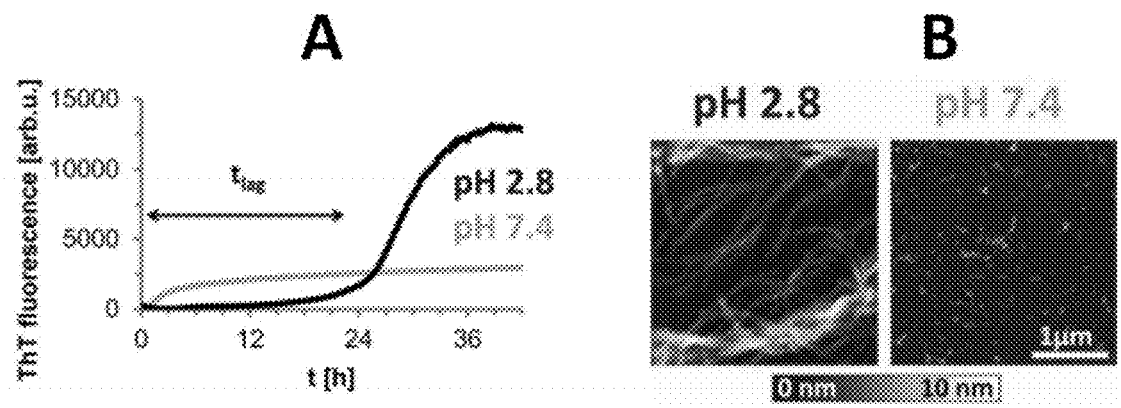

FIG. 6A. Aggregation kinetics of k-AL1 LC at neutral and acidic pH. FIG. 6B. LC fibrils were deposited on mica and imaged by atomic force microscopy; scale bar 1 µm, height scale 10 nm. Of note, urine derived LC form fibrils that stain positive with Thioflavin T and have typical amyloid morphology.

Figure 7:
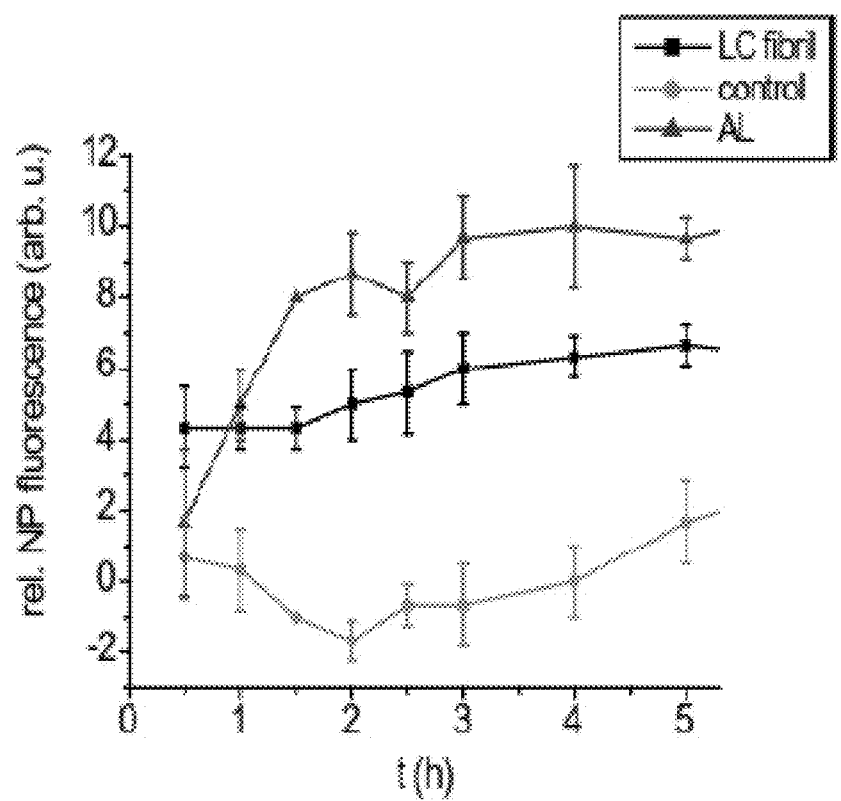

FIG. 7. LC amyloid detection in urine samples. LC isolated from AL patient shows increased nanoparticle fluorescence compared to control urine. LC was isolated from urine samples (500 µl) from an AL amyloidosis patient (AL), from a healthy control (control) and from control urine spiked with 50 µg AL-LC fibrils (LC fibril) by a two-step microfiltration protocol. Urine samples were treated with GdnHCl (3M) for 30 min, LC was separated from albumin by membrane filtration (50 kD cut-off). GdnHCl and small molecule contaminants were removed by membrane filtration (3x, 3 kD cut-off), and samples were incubated with Au-NP-194 nanoparticles (10 nM) in Na-phosphate buffer (20 mM, pH 7.4; NaCl, 150 mM; DTT, 10 mM) at 37° C. NP fluorescence was measured in a fluorescence microplate reader. Plotted are average fluorescence intensities (±SD) relative to the initial fluorescence signal. The experiment was performed using Au-NP-194 nanoparticles and urine samples of AL patients. Following demonstration of the disclosed probe to detect LCs in urine of AL patients, validation of this method in larger number of urine samples from AL and MM patients will be performed compared with controls, then test the efficacy of this test in a blind study.

DETAILED DESCRIPTION OF THE INVENTION

Figure 1:
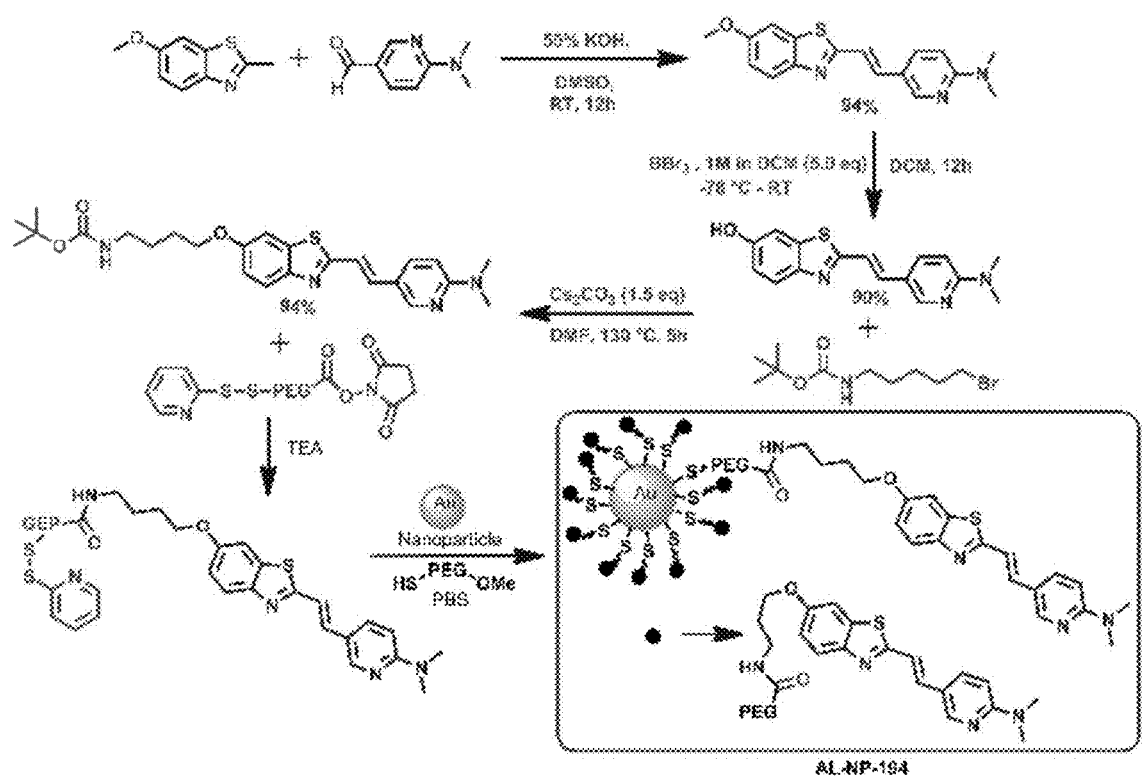
FIG. 1. Chemical Synthesis of Au-NP-194.

The present disclosure is based, at least in part, on the discovery of agents comprising small organic heterocyclic molecules capable of traversing the blood-brain barrier, and permeating the brain to label Aβ plaques in brains detect both diffuse and fibrillary plaques, wherein the diffuse plaques represent the precursor ligand to toxic compact plaques. While exploring chemical space for targeting other amyloidenic proteins, a water-soluble novel gold-nanoparticle conjugate Au-NP-194 was synthesized and characterized (see e.g., FIG. 1). As shown herein, the lead agent demonstrates unprecedented high affinity for LC aggregates, detects LC aggregates in autopsy samples, while also indicating its ability to detect LC aggregates at low concentrations in urine samples of AL patients.

Multiple myeloma (MM) represents a malignancy of terminally differentiated B lymphocytes, characterized by the expansion of clonal plasma cells in the bone marrow resulting in suppression of normal hematopoiesis, production of monoclonal immunoglobulins or their fragments (light or heavy chain), immunosuppression, nephropathy and neuropathy. Literature precedents indicate that 12-15% of MM patients develop overt clinical amyloidosis during the course of the disease, while approximately 30% MM patients are found to have subclinical amyloid deposits in subcutaneous fat pad aspirates, bone marrow biopsies, and heart, liver, and kidneys biopsies. Importantly, emerging clinical paradigms mandate to ascertain the presence of AL amyloidosis in multiple myeloma patients, prior to their stratification for a particular mode of therapeutic intervention.

Amyloid is an extracellular deposit of autologous proteins and is normally characterized by the presence of a characteristic apple-green birefringence, under polarized light following Congo red staining. Electron microscopy studies also reveal the amyloid protein to be comprised of rigid unbranched aggregates of fibrils of indefinite length. These fibrils consist of proteins arranged in anti-parallel, cross β-pleated sheet configuration with strands perpendicular to the long axis of the filament. Furthermore, these amyloid deposits are known to be resistant to proteolytic degradation thus induce toxicity by impacting normal physiological functions of critical organs, such as kidney, heart, liver, spleen, lung, gastrointestinal tract, skin and peripheral nerve. Although biochemical mechanisms involved in damages to organs are not completely known, and are intensely investigated; the organ dysfunction can potentially be reversible following regression of amyloid deposits.

The most common form of amyloidosis (outside the brain) is AL amyloidosis and results from accumulation and deposition of light chain immunoglobulin or rarely a fragment of a heavy chain. In most instances, the disease is systemic although localized amyloidosis involving the urinary tract, tracheobronchial tree, conjunctiva and thyroid are also well known.

Overall, clinical studies indicate that AL amyloidosis and multiple myeloma share common biochemical pathways, such as clonal plasma cells and the production of monoclonal immunoglobulins; however, the hallmark of the amyloid monoclonal light chain is its propensity to form insoluble fibrils with specific tropism in variable organs. Therefore, the diagnosis of AL amyloidosis requires histological confirmation of a biopsy specimen staining positive with Congo red exhibiting apple green birefringence under polarized light. Of note, a concurrent diagnosis of AL amyloidosis is made at presentation or sometime during the development of the MM in 10-15% of patients. Therefore, the diagnostic criteria for both conditions include histological confirmation of amyloid fibrils deposition and other myeloma-specific criteria, such as hypercalcemia, lytic bone lesions and anemia. However, Congo red negative yet MM positive cases have been frequently encountered in clinics. Present detection techniques also include laser induced micro-dissection of biopsies, and confirmation of either presence or absence of LCs (light chains) using a LCMS, an invasive technique confined to 3-4 US institutions for confirmation of AL amyloidosis in MM patients.

Therefore, the differentiation between MM and AL patients remains an urgent unmet need in routine diagnostics.

Present techniques for confirmation of AL amyloidosis in MM patients which include laser induced micro-dissection of biopsies and confirmation of either presence or absence of light chains (LCs) using mass spectrometry are invasive, and are confined to 3-4 US institutions thus limiting their access.

Therefore, diagnostic agents capable of enabling noninvasive detection of AL amyloidosis and its correlation with MM would allow stratification of MM patients for therapeutic interventions, are urgently mandated, and continues to be an unmet goal in the management of AL and MM.

Figure 2:
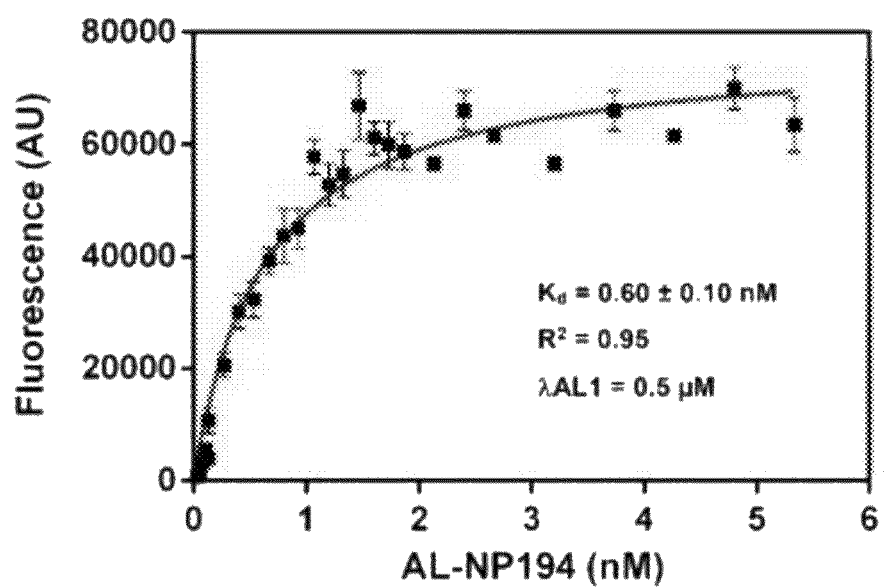
FIG. 2. Binding affinity of Au-NP194 (lab Coding: AL-NP194) with LC aggregates. The light chain aggregates (0.5 µM) were incubated for 30 min at 37° C. and fluorescence spectra were recorded (excitation 435 nm, emission 450-550 nm). Blank spectra of light chain in PBS were subtracted to correct for light scattering by the amyloid. Signals of unbound nanoparticles at equivalent concentrations were subtracted. The data were fitted by an equation for single site binding: $F=Bmax*c/(KD+c)$ from which a KD of 0.6±0.1 nM was calculated.
Figure 3:
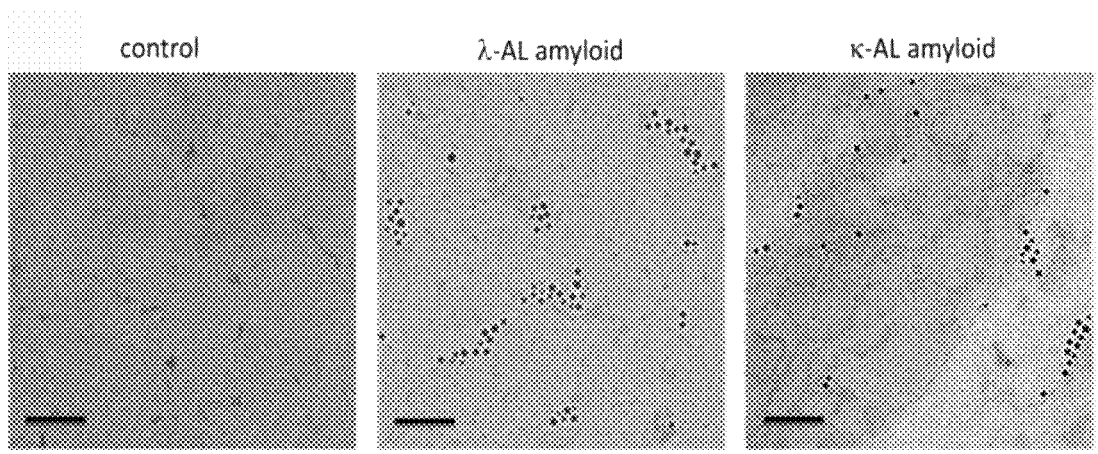
FIG. 3. Electron microscopy of Au-NP-194 binding to λ AL and κ AL light chains. AL light chains (25 µM) were aggregated for 21 d (glycine buffer pH 2.8, 150 nM NaCl), deposited on a carbon coated copper grid, stained with Au-NP-194 (8.4 nM), washed with buffer and UAR negative staining; scale bar 100 nm. Of note, Au-NP-194 demonstrates excellent specific staining at sub-nanomole concentrations indicating high sensitivity of the probe for AL light chains.
Figure 4:
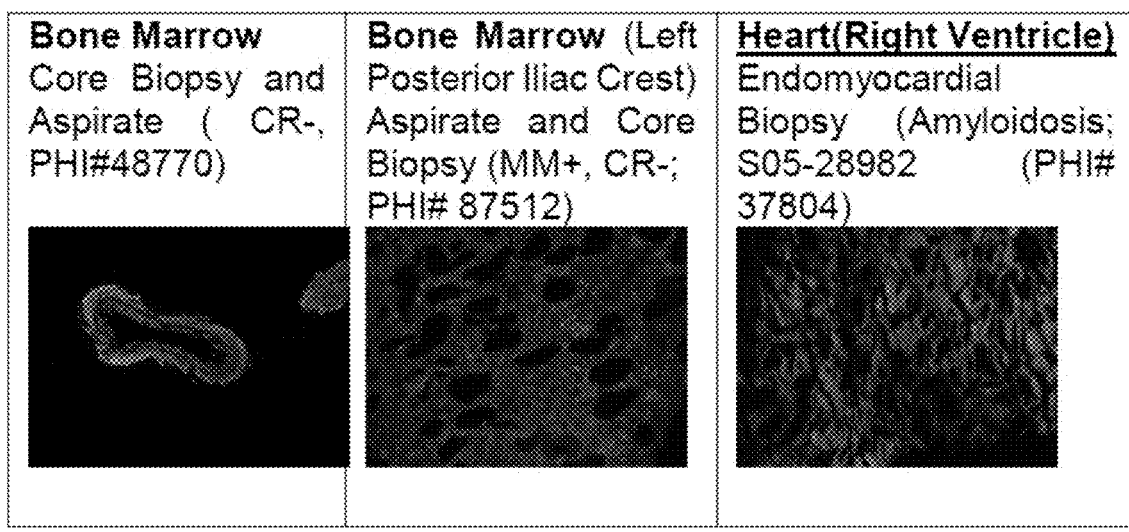
FIG. 4. Histochemical staining of human biopsy specimens. Sections (5 µm, n=4) were deparaffinized and incubated with Au-NP-194 (20 nM) for 30 min, rinsed with PBS-Triton-X-100, mounted, dried, cover slipped, and analyzed using Nikon Eclipse E800 epifluorescence microscope. CR; Congo Red; data not shown). Of note, Au-NP-194 exhibits sensitivity to probe amyloidosis in biopsied specimens.

The incidence of AL amyloidosis is about 8 million per year, making AL the most prevalent form of amyloid disease outside the central nervous system in developed countries. Approximately, 15% of MM patients share common criteria with AL amyloidosis patients. In AL amyloidosis, fibrils are formed from a part or the whole N-terminal variable domain of monoclonal kappa or lambda light chains, and are deposited in the organs and tissues. The accumulation of amyloid can be confined into a particular organ (localized) or throughout the body (systemic). Therefore, diagnostic agents capable of probing presence or absence of amyloidosis (both systemic and localized) in vivo would be beneficial in stratification of patients. These agents would facilitate the optimal selection of a given therapeutic intervention and also assist in evaluating therapeutic efficacy of existing or upcoming therapeutic regimens. Current methodologies for detecting AL amyloidosis are confined to a simple detection of amyloid with Congo red dye in biopsied specimens and laser induced micro-dissection of biopsied specimens coupled to mass spectrometry for confirmation of those light chain proteins. The former technique is difficult to interpret and lacks clarity, generates false negatives and thus needs to be supported with other biomarkers (monoclonal immunoglobin proteins) in serum or urine. The latter (the more quantitative and precise method) is restricted to only a few sophisticated centers worldwide thus restricting widespread access for confirmation of AL amyloidosis. PET imaging can enable noninvasive diagnostic assessment of both localized and systemic amyloidosis. Recently, Aβ PET imaging agents have been evaluated for AL imaging.[22,23] Due to inherent limitation in their molecular design for detecting several macroproteins encompassing β-sheet structure, while they show strong structural specificity they lack molecular specificity.[26] Unfortunately, ultrasensitive and specific PET agents capable of quantifying amyloid burden mediated by LC in vivo have not been discovered to-date. To accomplish this objective, a lead gold-nanoparticle conjugate that binds to light chain aggregates with unprecedented high affinity and specificity was identified (see e.g., FIG. 2, FIG. 3); demonstrated by its ability to detect AL in biopsied specimens from bone marrow aspirates and cardiac tissues (see e.g., FIG. 4), while also indicating its ability to detect light chains in urine samples of AL patients (see e.g., FIG. 7).

A PET ligand and a clinically viable cost-efficient test (which provides complementary information on renal function of AL/MM patients) directly from urine can be beneficial for stratification of therapeutic efficacy of new therapeutic interventions.

Molecular Imaging Probes for Specific Detection AL Amyloid in Amyloidosis and Multiple Myeloma Patients Light Chain Amyloidosis (AL Amyloid)

Light chain amyloidosis (AL amyloid) is a unique disease characterized by the deposition of a relatively insoluble protein (amyloid) into the organs and tissue of the affected patient. It is the most common type of amyloidosis. One of the things that differentiates AL amyloid from other cancers is that it is the deposited protein that is responsible for organ dysfunction and eventually patient death rather than the tumor cells themselves. The most commonly involved organs are the heart, kidneys, gastrointestinal tract, and nervous system, but any organ system can be involved. Because the organ systems involved can vary so much between patients and the extent of organ dysfunction can also be different, ascertaining diagnosis and prescribing a treatment plan requires a truly multidisciplinary team to diagnose and treat these complicated patients. In addition to patients with AL amyloid, up to 15% of patients with a related cancer, multiple myeloma (MM), develop light chain amyloid deposition.

One of the major difficulties in making the diagnosis of AL amyloid involves confirming that the patient has tissue involvement with amyloid, and then ascertaining that the subtype of amyloid is AL rather than one of the many other types of amyloid. Currently this requires doing biopsies of tissues such as the bone marrow, heart, kidneys, nerves, liver, GI tract, skin, etc. Currently, definitive confirmation of AL amyloidosis in patients includes laser micro-dissection of biopsies (obtained via invasive and often complicated procedures) using mass spectrometry, and access is confined to 3-4 US institutions, thus incurring wait-times of weeks to a month or more prior to confirmation. This leads to significant delays in starting therapy for these patients who can suffer clinical declines during this timeframe.

Therefore, ultrasensitive and specific diagnostic technologies are required for: a) determining the presence of AL amyloidosis in patients for stratification of therapeutic choices and b) assess therapeutic efficacy of drugs discovered for treatment of AL amyloidosis. One focus of the disclosed studies were focused on the development a rapid method of AL amyloid diagnosis with confirmation of the AL subtype (with less need for an invasive tissue biopsy) such as detection from the blood, urine, or a bone marrow specimen.

Diagnostic Technology

To diagnose AL amyloidosis, the present disclosure provides for the designed of a highly potent molecular imaging probe, which enables a sensitive and specific detection of AL in biological sample (e.g., urine or serum samples) of MM and Amyloidosis patients. This technology platform can also be conceptualized and developed for detection of AL in serum samples of patients. Importantly, both urine and serum samples are routinely collected during clinical visits of patients, and do not require tissue biopsy. Of note, our disclosed molecular imaging probe is also highly fluorescent, thus it can enable histopathological evaluation of biopsied samples. Following its further biochemical validation, it could also afford an alternative to Congo-Red staining of histopathological samples. It can also be extended to PET imaging probes to afford noninvasive detection of AL in MM and amyloidosis patients.

Here, is shown the potential of our new molecular imaging probe to detect the presence of light chain aggregates as well as aggregation-prone light chains directly in urine and serum samples of MM and cardiac amyloidosis patients which can be used for a clinically viable, yet cost-efficient test. The sensitive and economically viable clinical test can be conducive to current healthcare reimbursement models for detecting low concentrations of light chain aggregates in urine and serum samples of MM patients. Importantly, both tests can offer cost-efficient diagnostic tools for assessing efficacy of therapeutics in patients undergoing treatments.

Of note, the platform technology developed for the urine and serum tests can also lay the methodical foundation for detection of AL aggregates, using PET imaging in the near future. PET imaging would allow another method of noninvasive and specific detection of AL in MM and amyloidosis patients. In addition to helping detect which organs are infiltrated by amyloid, PET imaging can finally offer the opportunity to quantify the amount of tissue involvement and track regression or progression of amyloid deposition over time using a noninvasive imaging technique.

Imaging Agent

The imaging agent as described herein is an anti-amyloid nanoparticle comprising a nanoparticle, a linker, and a small organic heterocyclic molecule capable of binding light chain (LC) aggregates. Furthermore, the imaging agent or nanoparticle can incorporate a radiolabel or a fluorophore.

Imaging can include PET or SPECT, because 'cold' gold can be swapped with 'hot' gold (Au-189 and Au-198). And because AL is a systemic disease, both PET and SPECT tracers are useful. While PET can be beneficial for more acute short term quantitative imaging, SPECT can be beneficial for delayed imaging more conducive with normal pharmacokinetic profiles of nanoparticles.

Radiolabel

One embodiment of the present disclosure provides for a radiolabeled imaging agent, composition, or a composition with a radionuclide.

References herein to "radiolabeled" include a compound where one or more atoms are replaced or substituted by an atom having an atomic mass or mass number different from the atomic mass or mass number typically found in nature (i.e., naturally occurring). One non-limiting exception is $^{19}$F, which allows detection of a molecule which contains this element without enrichment to a higher degree than what is naturally occurring. Compounds carrying the substituent $^{19}$F may thus also be referred to as "labelled" or the like. The term radiolabeled may be interchangeably used with "isotopically-labelled", "labelled", "isotopic tracer group", "isotopic marker", "isotopic label", "detectable isotope", or "radioligand".

In one embodiment, the compound comprises a single radiolabeled group.

Examples of suitable, non-limiting radiolabel groups can include: $^{199}$Au, $^{198}$Au, $^{2}$H (D or deuterium), $^{3}$H (T or tritium), $^{11}$C, $^{13}$C, $^{14}$C, $^{64}$Cu, $^{67}$Cu, $^{177}$Lu, $^{13}$N, $^{15}$N, $^{15}$O, $^{17}$O, $^{18}$O, $^{18}$F, $^{89}$Sr, $^{35}$S, $^{153}$Sm, $^{36}$Cl, $^{82}$Br, $^{75}$Br, $^{76}$Br, $^{77}$Br, $^{123}$I, $^{124}$I, $^{125}$I, $^{131}$I, $^{111}$In, $^{67}$Ga, $^{68}$Ga, $^{177}$Lu, $^{186}$Re, $^{188}$Re, $^{201}$Tl $^{99m}$Tc, $^{90}$Y, or $^{89}$Zr. For example, the radiolabel can be $^{64}$Cu. It is to be understood that an isotopically labeled compound needs only to be enriched with a detectable isotope to, or above, the degree which allows detection with a technique suitable for the particular application, e.g., in a detectable compound labeled with $^{11}$C, the carbon-atom of the labeled group of the labeled compound may be constituted by $^{12}$C or other carbon-isotopes in a fraction of the molecules. The radionuclide that is incorporated in the radiolabeled compounds will depend on the specific application of that radiolabeled compound. For example, "heavy" isotope-labeled compounds (e.g., compounds containing deuterons/heavy hydrogen, heavy nitrogen, heavy oxygen, heavy carbon) can be useful for mass spectrometric and NMR based studies. As another example, for in vitro labelling or in competition assays, compounds that incorporate $^{3}$H, $^{14}$C, or $^{125}$I can be useful. For in vivo imaging applications $^{11}$C, $^{13}$C, $^{18}$F, $^{19}$F, $^{120}$I, $^{123}$I, $^{131}$I, $^{75}$Br, or $^{76}$Br can generally be useful.

Nanoparticle

As described herein, any nanoparticle suitable for use can be used in an imaging agent (e.g., SPECT, PET, fluorescence). For example, the imaging agent can incorporate a fluorophore or a radiolabel. A radiolabel can be doped in or on a nanoparticle, or a radiolabel can be conjugated to the imaging agent via, for example, the nanoparticle.

The imaging agent, as described herein can comprise any nanoparticle known in the art suitable for use as an imaging agent. Nanoparticles for use in molecular probes and imaging agents are well known; see e.g., Chen et al., Molecular Imaging Probes for Cancer Research, 2012.

Labeling of nanoparticles are well known; see e.g., Yongjian Liu, Michael J Welch, Nanoparticles labeled with positron emission nuclides: advantages, methods, and applications, Bioconjugate Chemistry, 2012, 23, 671-682; Stockholf et al., Pharmaceuticals (Basel). 2014 April; 7 (4): 392-418. Except as otherwise noted herein, therefore, the process of the present disclosure can be carried out in accordance with such processes.

For example, a nanoparticle can be a nanocluster or any other type of nanostructures including organic, inorganic, or lipid nanostructures.

As another example, the nanoparticle can comprise Au (which can comprise $^{199}$Au, $^{198}$Au) or Cu (which can comprise $^{64}$Cu). As another example, the nanoparticle can comprise iron oxide, gold, gold nanoclusters (AuNC), gold nanorods (AuNR), copper (Cu), quantum dots, carbon nanotubes, carbon nanohorn, gadolinium (Gd), dendrimers, dendrons, polyelectrolyte complex (PEC) nanoparticles, calcium phosphate nanoparticles, perfluorocarbon nanoparticles (PFCNPs), or lipid-based nanoparticles, such as liposomes and micelles.

As another example, gold nanoparticles were disclosed herein and can be converted to copper, for radiolabeling to use as a diagnostic with copper-64.

Linker

Described herein are linkers used to attach a heterocyclic small molecule to a portion of an imaging agent (e.g., a core, a nanoparticle, a radiolabel, a chelator, another peptide). A linker can be any composition used for conjugation, for example to a nanoparticle or chelator.

A linker group can be any linker group suitable for use in an imaging agent. Linker groups for imaging agents (e.g., molecular probes) are well known (see e.g., Werengowska-Ciećwierz et al., Advances in Condensed Matter Physics, Vol. 2015 (2015); Chen et al., Curr Top Med Chem. 2010; 10(12): 1227-1236). Except as otherwise noted herein, therefore, the processes of the present disclosure can be carried out in accordance with such processes.

For example, the linker can conjugate a nanoparticle to a small organic heterocyclic molecule. For example, a small organic heterocyclic molecule can be covalently attached to the linker. For example, the linker can comprise a poly (ethylene glycol) (PEG) or a derivative thereof. As another example, the linker can comprise PEG, TA-PEG-Maleimide, TA-PEG-OMe, or TA-PEG. As another example, a linker can comprise an isothiocyanate group, a carboxylic acid or carboxylate groups, a dendrimer, a dendron, Fmoc-protected-2,3-diaminopropanoic acid, ascorbic acid, a silane linker, minopropyltrimethoxysilane (APTMS), or dopamine. Other covalent coupling methods can use employ the use of 2 thiol groups, 2 primary amines, a carboxylic acid and primary amine, maleimide and thiol, hydrazide and aldehyde, or a primary amine and aldehyde. For example, the linker can be an amide, a thioether, a disulfide, an acetyl-hydrazone group, a polycyclic group, a click chemistry (CC) group (e.g., cycloadditions, for example, Huisgen catalytic cycloaddition; nucleophilic substitution chemistry, for example, ring opening of heterocyclic electrophiles; carbonyl chemistry of the "nonaldol" type, for example, formation of ureas, thioureas, and hydrazones; additions to carbon-carbon multiple bonds, for example, epoxidation and dihydroxylation); or a physical or chemical bond.

Small Organic Heterocyclic Molecules

Examples of imaging agents are described herein. Imaging agents can comprise a heterocyclic, wherein the heterocyclic molecule has affinity for amyloid-based aggregates comprising beta-sheet structures. The high-affinity heterocyclic molecules can have a Kd of about 600 pmol or less.

The heterocyclic molecule can have the formula:

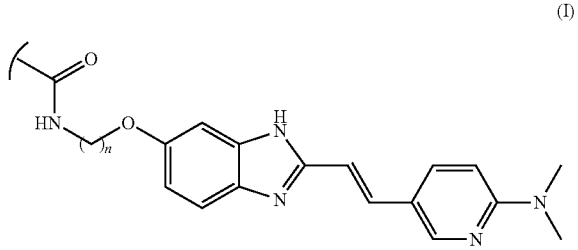

(I)

or a derivative, pharmaceutically acceptable salt, solvate or polymorph thereof, including all tautomers and stereoisomers thereof, wherein n=3 or 4. Derivatives can include substitutions anywhere on formula (I), substitutions of C, N, O, or substitutions of alkyl groups.

Formula (i) can be optionally substituted by R groups. The R groups can be optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; a $C_{2-6}$cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; straight chain or branched $C_{1-10}$alkyl amine, optionally containing unsaturation; a $C_{2-6}$cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; hydroxyl; amine; $C_{1-10}$carboxylic acid; $C_{1-10}$carboxyl straight chain or branched $C_{1-10}$alkyl, optionally containing unsaturation; straight chain or branched $C_{1-10}$alkyl amine, optionally containing unsaturation; a $C_{1-6}$cycloalkyl optionally containing unsaturation or one oxygen or nitrogen atom; heterocyclyl; straight chain or branched $C_{1-10}$alkyl amine; heterocyclic amine; and aryl comprising a phenyl; and heteroaryl containing from 1 to 4 N, O, or S atoms. Any of the above can be further optionally substituted.

The term "imine" or "imino", as used herein, unless otherwise indicated, includes a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, includes —OH. The "hydroxyl" can be optionally substituted.

The terms "halogen" and "halo", as used herein, unless otherwise indicated, include a chlorine, chloro, Cl;, fluorine, fluoro, F; bromine, bromo, Br; or iodine, iodo, or I.

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of aryl groups include, but are not limited to, phenyl, benzyl, naphthyl, or anthracenyl. The "aryl" can be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, includes saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated C1-C8 alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or-3-methyl-1 butynyl. An alkyl can be saturated, partially saturated, or unsaturated. The "alkyl" can be optionally substituted.

The term "carboxyl", as used herein, unless otherwise indicated, includes a functional group consisting of a carbon atom double bonded to an oxygen atom and single bonded to a hydroxyl group (—COOH). The "carboxyl" can be optionally substituted.

The term "alkenyl", as used herein, unless otherwise indicated, includes alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, includes alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, includes a functional group derived from an aliphatic carboxylic acid, by removal of the hydroxyl (—OH) group. The "acyl" can be optionally substituted.

The term "alkoxyl", as used herein, unless otherwise indicated, includes O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl and —O-cyclodecyl, —O—CH$_2$-cyclopropyl, —O—CH$_2$-cyclobutyl, —O—CH$_2$-cyclopentyl, —O—CH$_2$-cyclohexyl, —O—CH$_2$-cycloheptyl, —O—CH$_2$-cyclooctyl, —O—CH$_2$-cyclononyl, —O-CH$_2$-cyclodecyl, —O—(CH2)2-cyclopropyl, —O—(CH$_2$)$_2$-cyclobutyl, —O—(CH$_2$)$_2$-cyclopentyl, —O—(CH2)2-cyclohexyl, —O—(CH$_2$)$_2$-cycloheptyl, —O—(CH$_2$)$_2$-cyclooctyl, —O—(CH$_2$)$_2$-cyclononyl, or —O—(CH$_2$)$_2$-cyclodecyl. An alkoxyl can be saturated, partially saturated, or unsaturated. The "alkoxyl" can be optionally substituted.

The term "cycloalkyl", as used herein, unless otherwise indicated, includes a non-aromatic, saturated, partially saturated, or unsaturated, monocyclic or fused, spiro or unfused bicyclic or tricyclic hydrocarbon referred to herein containing a total of from 3 to 10 carbon atoms, preferably 3 to 8 ring carbon atoms. Examples of cycloalkyls include, but are not limited to, C3-C8 cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. The term "cycloalkyl" also includes -lower alkyl-cycloalkyl, wherein lower alkyl and cycloalkyl are as defined herein. Examples of -lower alkyl-cycloalkyl groups include, but are not limited to, —CH$_2$-cyclopropyl, —CH$_2$-cyclobutyl, —CH$_2$-cyclopentyl, —CH$_2$-cyclopentadienyl, —CH$_2$-cyclohexyl, —CH$_2$-cycloheptyl, or —CH$_2$-cyclooctyl. The "cycloalkyl" can be optionally substituted.

The term "heterocyclic" or "heteroaryl", as used herein, unless otherwise indicated, includes an aromatic or non-aromatic cycloalkyl in which one to four of the ring carbon atoms are independently replaced with a heteroatom from the group consisting of O, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "hetreocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, includes a —CN group. The "cyano" can be optionally substituted.

The term "alcohol", as used herein, unless otherwise indicated, includes a compound in which the hydroxyl functional group (—OH) is bound to a carbon atom. In particular, this carbon center should be saturated, having single bonds to three other atoms. The "alcohol" can be optionally substituted.

The term "solvate" is intended to mean a solvate form of a specified compound that retains the effectiveness of such compound. Examples of solvates include compounds of the invention in combination with, for example: water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating AL amyloidosis or Multiple Myeloma (MM) with or without AL amyloidosis in a subject in need administration of a therapeutically effective amount of a therapeutic agent, so as to treat AL amyloidosis or Multiple Myeloma (MM) with or without amyloidosis.

Methods described herein are generally performed on a subject in need thereof. A subject in need of the therapeutic methods described herein can be a subject having, diagnosed with, suspected of having, or at risk for developing AL amyloidosis or Multiple Myeloma (MM) with or without amyloidosis. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a therapeutic agent is, for example, that amount that would cause the desired therapeutic effect in a subject while minimizing undesired side effects. In various embodiments, an effective amount of a therapeutic agent described herein can substantially inhibit AL amyloidosis or Multiple Myeloma (MM) with or without amyloidosis, slow the progress of AL amyloidosis or Multiple Myeloma (MM) with or without amyloidosis, or limit the development of AL amyloidosis or Multiple Myeloma (MM) with or without amyloidosis.

MM treatment can include chemotherapy, blood transfusion, steroid, bone health drugs, or autotransplantation. Light-Chain (AL) Amyloidosis treatment can include rapid reduction of the supply of amyloidogenic monoclonal light chains by suppressing the underlying plasma cell dyscrasia. For example, and depending on the organs implicated, AL treatment can include sodium restriction and the careful administration of diuretics, afterload reduction with angiotensin-converting enzyme inhibitors, norepinephrine, treatment of hyperlipidemia, angiotensin-converting enzyme inhibitors, angiotensin receptor blockers, hemodialysis, or peritoneal dialysis.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a therapeutic agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit AL amyloidosis or Multiple Myeloma (MM) with or without amyloidosis, slow the progress of AL amyloidosis or Multiple Myeloma (MM) with or without amyloidosis, or limit the development of AL amyloidosis or Multiple Myeloma (MM) with or without amyloidosis.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shamel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a therapeutic agent can occur as a single event or over a time course of treatment. For example, a therapeutic agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for substantially inhibiting AL amyloidosis or Multiple Myeloma (MM) with or without amyloidosis, slowing the progress of AL amyloidosis or Multiple Myeloma (MM) with or without amyloidosis, or limiting the development of AL amyloidosis or Multiple Myeloma (MM) with or without amyloidosis.

A therapeutic agent can be administered simultaneously or sequentially with another agent, such as an antibiotic, an anti-inflammatory, or another agent. For example, a therapeutic agent can be administered simultaneously with another agent, such as an antibiotic or an anti-inflammatory. Simultaneous administration can occur through administration of separate compositions, each containing one or more of a therapeutic agent, an antibiotic, an anti-inflammatory, or another agent. Simultaneous administration can occur through administration of one composition containing two or more of a therapeutic agent, an antibiotic, an anti-inflammatory, or another agent. A therapeutic agent can be administered sequentially with an antibiotic, an anti-inflammatory, or another agent. For example, a therapeutic agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Discovery, Validation, and Preclinical Development of a Pet Tracer

The following example describes the discovery, validation, and preclinical development of a PET tracer for imaging AL amyloidosis in vivo and a clinically viable test for the detection of immunoglobin proteins directly in urine samples, both of which are based on a nanoparticle with an unparalleled affinity for amyloid structures. Following identification of a lead scaffold with unprecedented binding affinity to light chain aggregates, conversion of the gold nanoparticle conjugate into a biodegradable copper-nanoparticle counterpart is not only innovative but represents an entirely novel strategy involving development of a biodegradable PET tracer for imaging AL amyloidosis in vivo with a dominant renal excretory pathway of excretion from the body. Additionally, incorporation of a $^{64}Cu$ radionuclide into the nanolattice makes it inert for in vivo applications compared with existing strategies involving chelation cores for coordinating radionuclides, the latter approach is susceptible to generation of competing radiometabolites thus resulting into inferior signal/noise ratios. Finally, PET agents with high molecular specificity and sensitivity to enable AL amyloidosis imaging have not been discovered to-date. Thus, the present disclosure represents a highly innovative initiative. Indeed, non-invasive diagnostic tools for AL are lacking, as is true for all amyloid diseases. First proof-of-concept studies based on the principle of in vitro replication of amyloid from blood and CSF are only just emerging for Alzheimer's disease and for prion diseases. This example discloses how to make this tool available to AL diagnosis from easily accessible urine, and translate the method to detect AL aggregates in other biological samples such as blood plasma.

While exploring structure-activity relationship (SAR) studies for detecting amyloid, a gold-nanoparticle conjugated to a fluorescent heterocyclic molecule (Au-NP-194) was recently identified that binds to light chain aggregates (extracted from urine of MM patients) in a concentration dependent manner with unprecedented high binding affinity (Kd=600 pmol). Additionally, the agent demonstrates specific binding to LC aggregates (electron microscopy), while also detecting the presence of amyloidosis in biopsied specimens of heart and bone marrow. Finally, Au-NP-194 also detects light chains in urine samples of AL patients.

Additional experiments to be performed include: (1) synthesize, characterize, and perform preclinical validation of $^{64}Cu$-labeled nanoparticles for noninvasive PET imaging of AL amyloidosis in vivo, using pharmacokinetic and imaging studies in mice, and determine their translational potential via autoradiography studies of biopsy specimens; and (2) assess potential of unlabeled Au-NP-194 to detect presence of LC aggregates as well as aggregation-prone light chains directly in urine of MM and cardiac amyloidosis patients compared with their control counterparts to develop a clinically viable yet cost-efficient test. While (1) will provide an opportunity to validate the PET tracer for imaging AL amyloidosis in vivo, (2) will allow for additional experiments for furthering the development of the cost-efficient sensitive test to detect low concentrations of light chain aggregates in urine of MM patients thus indicating AL pathology, while also assessing their relationships with glomerular abnormalities. Therefore, both techniques could provide complementary information in differential diagnosis of MM and AL. Of note, the platform technology developed for the urine test can be translated to the detection of AL aggregates in plasma. Both strategies can offer cost-efficient diagnostic tools for assessing efficacy of therapeutics in patients.

Small organic heterocyclic molecules capable of traversing the blood-brain barrier, and permeating the brain to label Aβ plaques in brains of transgenic mice were developed. These agents also detect both diffuse and fibrillary plaques, wherein the diffuse plaques represent the precursor ligand to toxic compact plaques. While exploring chemical space for targeting other amyloidenic proteins, a water-soluble novel gold-nanoparticle conjugate Au-NP-194 (see e.g., FIG. 1) was synthesized and characterized.

For bioassays, light chains were extracted from urine of AL and MM patients. Following their characterization, LC aggregates were prepared via incubation of the light chains (20 μM) in presence of DTT (10 mM) in PBS under continuous shaking at 37° C. for 48 h. Upon incubation of LC aggregates with Au-NP-194 in PBS, the nano-conjugate shows remarkably high fluorescence indicating its binding to aggregates (data not shown). To evaluate binding affinity, Au-NP-194 was incubated as a function of concentration with a fixed concentration of light chains (500 nM) for 30 min at 37° C. Au-NP-194 shows concentration dependent saturable binding. Employing a single site binding model (F=Bmax*c/(Kd+c)); the agent demonstrated an unprecedented high binding affinity (Kd=0.6 ±0.1 nM) (see e.g., FIG. 2). To further analyze specific interaction of Au-NP-194, λ AL and κAL light chains (25 mM) were aggregated for 21 d in the glycine buffer (pH 2.8), deposited on an EM grid, incubated with Au-NP-194 (8.6 nM), and washed with buffer. Compared with non-amyloid controls, TEM data shows specific labeling of λ AL light chain aggregates (see e.g., FIG. 3). To further take advantage of optical properties of the disclosed versatile probe, histochemical staining of human biopsy specimens were also performed. To ascertain its translational potential for labeling AL amyloid, biopsy specimens of human bone marrow aspirates and cardiac amyloidosis were used. For experiments, paraffin embedded specimens were cryosectioned to 5 μm (developmental biology, histology core facility, deparaffinized, and incubated with Au-NP-194 (20 nM) for 30 min, using well-established procedures. Importantly, Au-NP-194 (8.6 nM) demonstrated excellent ability to detect AL amyloid (see e.g., FIG. 4).

This data, allows for the synthesis and validation of a PET counterpart of Au-NP-194 via multiple in vivo preclinical studies for translation in humans following toxicology studies, while simultaneously validating the translational potential of native Au-NP-194 to detect presence of AL light chains in urine samples of patients.

Finally, Au-NP-194 also demonstrates ability to detect LC aggregates in urine samples of AL patient compared with that of control (see e.g., FIG. 7). These studies allow for extending to detection of LCs in serum sample of patients.

Example 2

$^{64}$Cu-Nanoparticle Synthesis, Characterization, and Preclinical Validation

The following example describes the synthesis, characterization, and preclinical validation of $^{64}$Cu-nanoparticles for noninvasive PET imaging of AL amyloidosis in vivo, using pharmacokinetic and imaging studies in mice, and determine their translational potential via autoradiography studies of biopsy specimens Historically, PET counterparts of nanoprobes have been synthesized and validated using chelator cores for incorporation of the radionuclide. Although a successful strategy, these probes are prone to dechelation or loss of radionuclide thus creating competing radiometabolites in challenging microenvironments in vivo. As described herein, the gold nanoparticle is converted into a $^{64}$Cu-conjugate thereby incorporating PET radionuclide into the nanocrystal lattice itself to enable biomedical imaging without competing metabolites in vivo.

Synthesis and Characterization of $^{64}$Cu-Au-NP-194 Probe

The disclosed synthetic strategy is based upon early breakthrough indicating utility of cation exchange reactions in ionic nanocrystals, wherein the anion sublattice remains intact thus allowing basic shapes of nanocrystals to be preserved following requisite cation exchange.[32] Preservation of the anionic framework during the cation exchange enables transformation of multicomponent nanoheterostructures, while conserving not only the size and shape but also compositional interface between the individual constituents. This synthetic strategy would make new PET probes virtually inert in complex microenvironments in vivo. Employing this strategy, $^{64}$Cu-nanocrystal alloys have been obtained.[33,34] Here is disclosed the synthesis and characterization of $^{64}$Cu-Au-NP-194, using nonradioactive gold chloride (HAuCl$_4$) and Cu(acac)$_2$ in the presence of $^{64}$CuCl$_2$ at 160° C. for 2 h, using oleylamine (a solvent and reductant) as described earlier.[34] Also, here is described the synthesis of biodegradable only $^{64}$Cu-Au-194 nanoparticles by using similar exchange reactions while also adding unlabeled CuCl$_2$ in addition to $^{64}$CuCl$_2$. To facilitate renal excretion and allowing superior signal-to-noise ratios during micro-PET imaging experiments, PEG1000[35] is incorporated between the nanocrystal and targeting motif to facilitate high contrast imaging of amyloidosis in vivo. All nanoprobes (both Copper-Au alloys and pure copper nano-lattice) will be characterized using standard analytical and radiochemical tools described earlier.[33,34,36]

Autoradiography and Histochemical Relationships

Using well-established procedures, sections of biopsied specimens will be incubated with $^{64}$Cu-Au-NP-194 in the presence or absence of unlabeled counterpart, air dried, and analyzed on phosphoimager to determine target specificity. For correlations of autoradiography data, sections will be also be incubated in the presence or absence of Congo red (+control) to evaluate whether or not the probe co-localizes with the control. The diagnosis of suspected AL amyloidosis, irrespective of organ involvement includes identification of the clonal disease and amyloid typing, the latter is a critical factor for stratification of therapeutic choices to induce amyloid clearance thus improving organ function. Therefore, specificity of the PET tracer for AL compared with ATTR and AA will be assessed by incubating biopsied sections with either $^{64}$Cu-Au-NP-194 (5 nM; binding) or $^{64}$Cu-Au-NP-194 (5 nM; plus unlabeled Cu-Au-NP-194, 1 μM; displacement) at room temperature for 1 h. Thereafter, sections will be washed at RT in 30 mM Tris-HCl pH 7.4 for 1 min, 70% ethanol/30 mM Tris-HCl for 2 min, 30% ethanol/30 mM Tris-HCl for 1 min and 30 mM Tris-HCl for 1 min. Following washings, the sections will be dried, and exposed to a phosphor imaging screen (BAS-TR 2025) for 45 min. Autoradiography images will be obtained on GE Typhoon System FLA-9500 (Tokyo, Japan) at 25 μm resolution. Data will be exported as linear 16-bit grayscale TIFF images and further processed by Adobe Photoshop CS3. For quantification of radiolabeling, count intensities (expressed as quantitative light unit (QL/pixel2) will also be measured in the target and reference regions. For immunohistochemistry (IHC), the same sections will be blocked for 60 min at room temperature with 3% milk-0.25% Tween20-PBS buffer. After a 1 min wash in 0.5% milk-PBS-0.25% Tween 20, the sections will be stained with either a monoclonal antibody directed against AA amyloid (Dako, Denmark), polyclonal antibodies directed against transthyretin (TTR), λ-LCs or κ-LCs, then visualized by secondary antibodies conjugated with fluorophores, using well-established methodologies.

Pharmacokinetic Studies in Mice

To evaluate pharmacokinetics, quantitative biodistribution studies in FVB mice (n=5) via tail-vein administration and mice will be sacrificed by cervical dislocation at 1 h, 6 h, 12 h, and 24 h. Critical organs (brain, lung, liver, spleen, kidney, muscle, heart, bone, marrow, stomach, and intestine) will be harvested rapidly. Blood samples will be obtained by cardiac puncture, and all tissue samples analyzed for γ-activity. Data are expressed as the percentage of injected dose (% ID) per gram of tissue (tissue kBq (injected kBq)$^{-1}$ (g tissue)$^{-1}$×100) as described.[36]

Transgenic Mice

Transgenic mice model for amyloidosis will be produced as described.[38] Briefly, a linear 2412 bp fragment of the pcDNA-AL080 λ6 plasmid containing the CMV promoter, λ6 LC gene, and bovine growth hormone (BGH) polyadenylation sequence will be produced by restriction enzyme digestion with BglII and XmnI.[38] Mice are injected pcDNA-AL080 λ6 plasmid DNA to simulate AL amyloidosis in human for analyzing potential of $^{64}$Cu-Au-NP-194 for PET imaging of amyloidosis and analyze therapeutic efficacy of doxycycline (3-6 months old, 0.5 mg/mL, treated for 7 months[38]) and NEOD001, a monoclonal antibody known to target amyloid in AL amyloidosis (3-6 months old, treated for 3 weeks). Alternatively, another transgenicH2/IL-6 mouse model[39] will be used for analysis of PET tracers.

MicroPET Imaging

MicroPET imaging will be performed either in the untreated transgenic mice or treated with drugs such as NEOD001 and Doxycycline with 1 h, 6 h, 12 h, and 24 h post intravenous tail-vein injection (22,200 kBq) of HPLC-purified $^{64}$Cu-Au-NP-194 radiopharmaceutical (95/5 saline/ethanol) using Inveon PET/CT scanner (Siemens Medical Solutions) as described.[36] For imaging, the transgenic mouse will be anesthetized with isoflurane, secured in a supine position and placed in an acrylic imaging tray. PET dynamic data will be acquired over 2 h starting immediately following injection of the tracer. The emission data will be normalized, corrected for attenuation, scatter, and decay. Attenuation correction will be obtained using the co-registered CT data. The image volume will consist of 256×256× 159 voxels, with a size of 0.39×0.39×0.8 mm$^3$ per voxel for the Inveon scanner. For anatomical visualization, PET images will be co-registered with CT images from an Inveon PET/CT scanner. For analysis, myocardium, liver, and kidney uptakes (Bq/mL) will be normalized to injected dose and weight of mice. To accomplish this aim, ROIs will be drawn over myocardium, liver, and kidney, counts will be normalized to % ID/g, and weight of the mice to obtain SUV values. All image data will be processed and analyzed using Inveon Research Workspace 4.1 software (Siemens).

Pharmacokinetics

While detection of LC aggregates in urine of MM patients provides us a unique opportunity to further validate this technology in larger group of patients compared with their control counterparts, the nanoparticle-based PET tracers could potentially show slow pharmacokinetics from organs possessing targeted LC aggregates thus potentially complicating PET imaging analysis. To address that obstacle upfront, an active fragment was designed with structural components enriched with nitrogen heteroatoms and dimethylamine substituents thus balancing octanol/water partitioning coefficient to facilitate excretion of unbound tracer from normal organs. These structural parameters embedded into the molecular design could be beneficial to overcome those limitations. This disclosure provides for the development of nanoPET tracers that would preferentially undergo renal modes of excretion. Upon penetration into glomerular capillary bed, a given probe can either be filtered through the glomerular capillary wall into the proximal tubule or could also remain within the vascular compartment. This trait is a complex function of molecular size, shape, surface modification, and charge. Literature precedents indicate that molecules possessing spherical shape, electrochemical neutrality under physiological conditions, and a hydrodynamic diameter (HD)<5 nm normally undergo facile renal mode of excretion. While molecular shape, charge, and optimal surface modification (activity fragment) is already conceived and embedded into the design of the nanoprobe, if encountered difficulties in terms of slow pharmacokinetics, molecular size would be decreased further below 5 nm. Finally, PET-radionuclide for incorporation into the probe design was carefully selected to allow imaging at later time points. To accomplish that objective, the incorporation of Cu-64 ($t_{1/2}$=12.7 h, a moderate half-life) into the design of the probe, further mitigates this risk, thus provides us a desired time frame for delayed imaging of targeted tissues following excretion of an unbound tracer.

Example 3

Unlabeled Au-NP194 Assessment

The following example describes the assessment of unlabeled Au-NP194 to detect presence of LC aggregates as well as aggregation-prone light chains directly in urine of MM and cardiac amyloidosis patients compared with their control counterparts to develop a clinically viable yet cost-efficient test.

AL is complication of myeloma that requires intervention by chemotherapy. AL can be diagnosed by symptoms, such as a widened left ventricle in the heart and swollen tongue, but nonspecific symptoms that are associated with AL amyloidosis often delay diagnosis. Furthermore, differentiation from non-amyloid multiple myeloma is difficult. A clear diagnosis of AL requires histological staining of amyloid deposits in the heart or in fat tissue. Sample acquisition therefore involves highly invasive tissue biopsies. An easy non-invasive test for AL from urine could facilitate diagnosis and enable earlier AL-specific treatment. Therefore, the potential of Au-NP-194 for detection of AL amyloid in patient urine as a tool in the differential clinical diagnosis of AL amyloidosis is evaluated.

Data

Figures 5A, 5B:
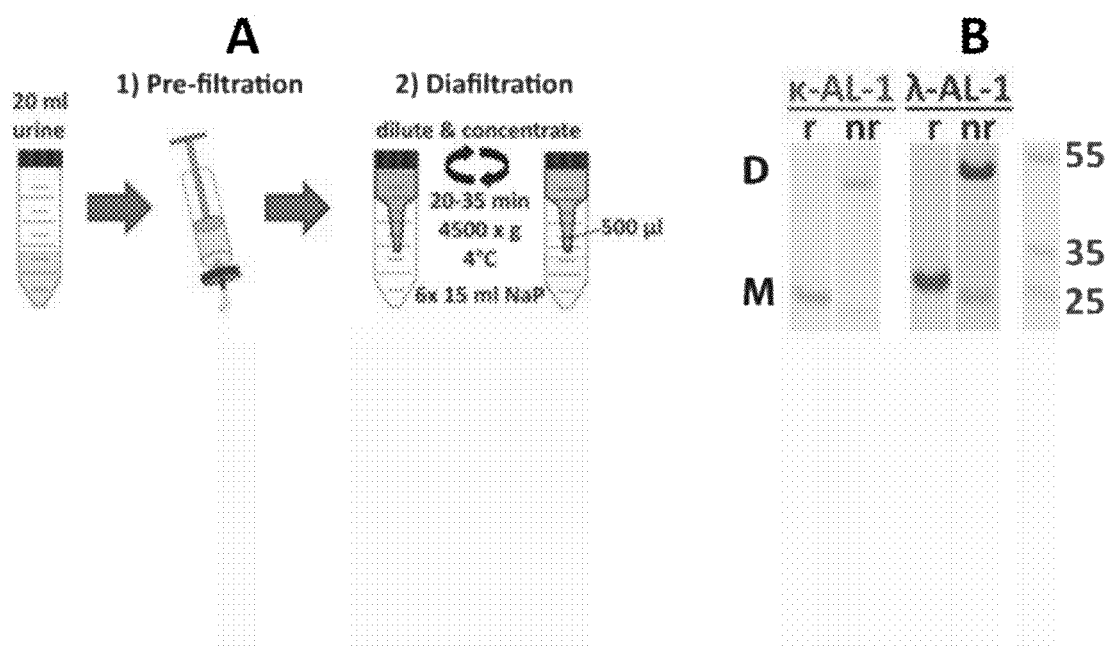
FIG. 5A-FIG. 5B. Purification of LC from AL patient urine.[29] FIG. 5A. Urine was cleared via sterile filtration, then small molecule contaminants were removed by diafiltration using a membrane concentrator.

Even before proteinuria sets in, MM and AL patients typically secrete LC at concentrations of 1 μg-1 mg/ml in their urine. In the context of a multicentric study on the efficacy of reducing amyloid load in AL by the natural polyphenol EGCG, a simple, two-step procedure to purify LC from the urine of MM and AL patients (see e.g., FIG. 5) is used. Patient urine is sterile filtered through a 0.2 μm membrane to enable safe handling. Then membrane diafiltration removes urea and other small molecules and brings the LC into a buffer suitable for nanoparticle detection, or for amyloid amplification. In these patients the procedure yielded LC with >90% purity. In these experiments, purification procedure to albumin that is present in urine was refined (see e.g., FIG. 7). AL-derived LC from urine form amyloid fibrils in vitro under reducing conditions that are detected with sub-nanomolar affinity by Au-NP-194 (see e.g., FIG. 2, FIG. 3).The buffer pH was varied to optimize conditions for LC aggregation. At pH 2.8 AL-LC formed well-ordered fibrils that bind the amyloidophilic dye Thioflavin T and present aggregation kinetics typical of amyloid fibril formation (see e.g., FIG. 6). This is significant, because albumin, which is another major constituent found in the urine of AL patients, does not form amyloid under these conditions.[40] Indeed, the disclosed data demonstrates ability of Au-NP194 to detect light chain aggregates in urine of AL patient compared with that of a control (see e.g., FIG. 7).

Experimental Methodology

As AL progresses, patient often present with proteinuria, in which LC, among other proteins, are secreted with the urine. These LC may already be present in the form of amyloid aggregates or they may be secreted as natively folded proteins that have an increased propensity to form amyloid aggregates, when compared to MM-LC. Based on these two alternatives, a two-pronged experimental approach is evaluated for its diagnostic potential in patient urine; Strategy A: direct detection of amyloid by anti-amyloid nanoparticles; Strategy B: amplification of AL amyloid through in vitro replication.

Direct Detection of LC Amyloid

Au-NP-194 nanoparticle will be added directly to LC isolated from urine of AL and MM patients or their control counterparts, and their binding to amyloid aggregates will be detected by Au-NP-194 fluorescence (excitation 440 nm, emission 480 nm) in a fluorescence microplate reader. In this scheme, detection sensitivity could be further increased 10-100-fold by performing the LC isolation from a 10 mL urine sample and then concentrating the NP by centrifugation and resuspending them in 100 µL prior to detection as described in (see e.g., FIG. 5, FIG. 7).

Amplification of LC Amyloid

To further enhance sensitivity, an amyloid amplification step is added prior to nanoparticle detection. Amyloid structure can be amplified in vitro through a mechanism of seeded growth.[41,42] Herein, rare amyloid aggregates serve as templates for the addition of monomeric protein to form new fibrils. Amyloid fragmentation, for example by mechanical agitation, then creates new seed to catalyze amyloid formation in an avalanche-like process akin to prion replication. The initial amount of seeds can then be calculated from the lag time ($t_{lag}$) of the amyloid formation process.[43,44] To amplify rare LC amyloid, the urine isolates will be incubated in fibrillation buffer (25 µM LC; 10 mM DTT, glycine buffer pH 2.8, 150 nM NaCl) to reproducibly form amyloid fibrils with a defined $t_{lag}$ (see e.g., FIG. 6). The monomeric LC present in the sample serves as the substrate for amyloid fibril formation, while rare AL amyloid particles seed the amplification process. The amount of LC amyloid will be quantified from $t_{lag}$ and from Au-NP-194 fluorescence amplitude using as a reference scale synthetic seeds derived from fibril formation in vitro. Alternatively, a fixed amount of recombinantly expressed monomeric LC will be added as substrate to seed from urine samples allowing amplification, under standardized conditions. The resulting AL amyloid will then be detected by Au-NP-194 nanoparticles as outlined in strategy A.

Additional Detection Methods

If detection by strategy A suffers from a lack of LC amyloid in urine, the following procedure can be followed. Amounts of LC in AL patient urine are typically 1 µg-1 mg/ml, corresponding to µM-mM concentration. Presumably even the low end of this spectrum will provide enough targeted protein for detection using the disclosed probe, which binds with sub-nanomolar affinity. In this experiment, AL-LC was easily detected, present in urine at 4 mM (see e.g., FIG. 7). However, the majority of LC may not be present as amyloid. This is the starting point for strategy B of amyloid amplification. LC amyloid amplification may be complicated by the abundance of other proteins, especially albumin. To overcome this complication, albumin is depleted by membrane filtration and perform the AL-specific amplification in vitro under buffer conditions that allow formation of LC amyloid but not of albumin.

REFERENCES

1. Merlini, G. & Bellotti, V. Molecular mechanisms of amyloidosis. N. Engl. J. Med. 349, 583-596, doi:10.1056/NEJMra023144 (2003).
2. Bellotti, V., Mangione, P. & Merlini, G. Review: immunoglobulin light chain amyloidosis—the archetype of structural and pathogenic variability. J. Struct. Biol. 130, 280-289, doi:10.1006/jsbi.2000.4248 (2000).
3. Chiti, F. & Dobson, C. M. Protein misfolding, functional amyloid, and human disease. Annu. Rev. Biochem. 75, 333-366, doi:10.1146/annurev.biochem.75.101304.123901 (2006).
4. Merlini, G. & Westermark, P. The systemic amyloidoses: clearer understanding of the molecular mechanisms offers hope for more effective therapies. J. Intern. Med. 255, 159-178 (2004).
5. Howlader, N., Ries, L. A., Stinchcomb, D. G. & Edwards, B. K. The impact of underreported Veterans Affairs data on national cancer statistics: analysis using population-based SEER registries. J. Natl. Cancer Inst. 101, 533-536, doi:10.1093/jnci/djn517 (2009).
6. Siegel, R., Ward, E., Brawley, O. & Jemal, A. Cancer statistics, 2011: the impact of eliminating socioeconomic and racial disparities on premature cancer deaths. CA. Cancer J. Clin. 61, 212-236, doi:10.3322/caac.20121 (2011).
7. Howlader, N. et al. SEER Cancer Statistics Review, 1975-2013, National Cancer Institute. Bethesda, MD. 2016http://seer.cancer.gov/statfacts/html/mulmy.html Accessed 13 Jun. 2016. (2016).
8. Kyle, R. A. & Rajkumar, S. V. Treatment of multiple myeloma: a comprehensive review. Clinical lymphoma & myeloma 9, 278-288, doi:10.3816/CLM.2009.n.056 (2009).
9. Kyle, R. A. et al. The treatment of multiple myeloma using vincristine, carmustine, melphalan, cyclophosphamide, and prednisone (VBMCP) alternating with high-dose cyclophosphamide and alpha(2)beta interferon versus VBMCP: results of a phase III Eastern Cooperative Oncology Group Study E5A93. Cancer 115, 2155-2164, doi:10.1002/cncr.24221 (2009).
10. Kyle, R. A. et al. Review of 1027 patients with newly diagnosed multiple myeloma. Mayo Clin. Proc. 78, 21-33, doi:10.4065/78.1.21 (2003).
11. Cavo, M. et al. International Myeloma Working Group consensus approach to the treatment of multiple myeloma patients who are candidates for autologous stem cell transplantation. Blood 117, 6063-6073, doi:10.1182/blood-2011-02-297325 (2011).
12. Giralt, S. et al. International myeloma working group (IMWG) consensus statement and guidelines regarding the current status of stem cell collection and high-dose therapy for multiple myeloma and the role of plerixafor (AMD 3100). Leukemia 23, 1904-1912, doi:10.1038/leu.2009.127 (2009).
13. Dispenzieri, A. et al. International Myeloma Working Group guidelines for serum-free light chain analysis in multiple myeloma and related disorders. Leukemia 23, 215-224, doi:10.1038/leu.2008.307 (2009).
14. Kumar, S. K. et al. Lenalidomide, cyclophosphamide, and dexamethasone (CRd) for light-chain amyloidosis: long-term results from a phase 2 trial. Blood 119, 4860-4867, doi:10.1182/blood-2012-01-407791 (2012).
15. Kumar, S. et al. Randomized, multicenter, phase 2 study (EVOLUTION) of combinations of bortezomib, dexamethasone, cyclophosphamide, and lenalidomide in previously untreated multiple myeloma. Blood 119, 4375-4382, doi:10.1182/blood-2011-11-395749 (2012).
16. Venner, C. P. et al. Cyclophosphamide, bortezomib, and dexamethasone therapy in AL amyloidosis is associated with high clonal response rates and prolonged progression-free survival. Blood 119, 4387-4390, doi:10.1182/blood-2011-10-388462 (2012).
17. Usnarska-Zubkiewicz, L. et al. Analysis of free serum light chains in patients suffering from multiple myeloma complicated by light-chain amyloidosis. Advances in clinical and experimental medicine: official organ Wroclaw Medical University 23, 531-538 (2014).

18. Dinner, S. et al. The prognostic value of diagnosing concurrent multiple myeloma in immunoglobulin light chain amyloidosis. Br. J. Haematol. 161, 367-372, doi:10.1111/bjh.12269 (2013).
19. Pinney, J. H. & Hawkins, P. N. Amyloidosis. Ann. Clin. Biochem. 49, 229-241, doi:10.1258/acb.2011.011225 (2012).
20. Pinney, J. H. & Lachmann, H. J. Systemic AA amyloidosis. Subcell. Biochem. 65, 541-564, doi:10.1007/978-94-007-5416-4_20 (2012).
21. Lachmann, H. J. & Hawkins, P. N. Systemic amyloidosis. Curr Opin Pharmacol 6, 214-220, doi:10.1016/j.coph.2005.10.005 (2006).
22. Antoni, G. et al. In vivo visualization of amyloid deposits in the heart with 11C-PIB and PET. J. Nucl. Med. 54, 213-220, doi:10.2967/jnumed.111.102053 (2013).
23. Wells, K. et al. 18F Florbetapir PET/CT cardiac amyloid imaging in patients with systemic amyloidosis. J. Nucl.Med. 54 (supplement 2), 294 (2013).
24. Lockhart, A. et al. PIB is a non-specific imaging marker of amyloid-beta (Abeta) peptide-related cerebral amyloidosis. Brain 130, 2607-2615 (2007).
25. Matias-Guiu, J. et al. Amyloid Proteins and Their Role in Multiple Sclerosis. Considerations in the Use of Amyloid—PET Imaging. Frontiers in neurology 7, 53 (2016).
26. Bodini, B. & Stankoff, B. Imaging Central Nervous System Demyelination and Remyelination by Positron-Emission Tomography. Brain Plasticity 2, 93-98 (2016).
27. Sundaram, G. et al. Characterization of a brain permeant fluorescent molecule and visualization of Aβ parenchymal plaques, using real-time multiphoton imaging in transgenic mice. Org. Lett. 16, 3640-3643 (2014).
28. Sundaram, G. S. et al. Synthesis, characterization, and preclinical validation of a PET radiopharmaceutical for interrogating Abeta (beta-amyloid) plaques in Alzheimer's disease. EJNMMI research 5, 112, doi:10.1186/s13550-015-0112-4 (2015).
29. Sundaram, G. et al. Fluselenamyl: A novel benzoselenazole derivative for PET detection of amyloid plaques (Aβ) in Alzheimer's disease. Scientific reports 6, 35636 (2016).
30. Andrich, K. et al. Aggregation of Full-length Immunoglobulin Light Chains from Systemic Light Chain Amyloidosis (AL) Patients Is Remodeled by Epigallocatechin-3-gallate. J. Biol. Chem. 292, 2328-2344, doi:10.1074/jbc.M116.750323 (2017).
31. Andrich, K. & Bieschke, J. The Effect of (-)-Epigallocatechin-(3)-gallate on Amyloidogenic Proteins Suggests a Common Mechanism. Adv. Exp. Med. Biol. 863, 139-161, doi:10.1007/978-3-319-18365-7_7 (2015).
32. Son, D., Hughes, S., Yoin, Y. & Alivisatos, A. Cation exchange reactions in ionic nanocrystals. Science 306, 1009-1012 (2004).
33. Sun, X. et al. Self-illuminating 64Cu-doped CdSe/ZnS nanocrystals for in vivo tumor imaging. J. Am. Chem. Soc. 136, 1706-1709, doi:10.1021/ja410438n (2014).
34. Zhao, Y. et al. Copper-64-alloyed gold nanoparticles for cancer imaging: improved radiolabel stability and diagnostic accuracy. Angew. Chem. Int. Ed. Engl. 53, 156-159, doi:10.1002/anie.201308494 (2014).
35. Zhao, Y., Sultan, D., Detering, L., Luehmann, H. & Liu, Y. Facile synthesis, pharmacokinetic and systemic clearance evaluation, and positron emission tomography cancer imaging of (6)(4)Cu-Au alloy nanoclusters. Nanoscale 6, 13501-13509, doi:10.1039/c4nr04569f (2014).
36. Sharma, V. et al. A Generator-Produced Gallium-68 Radiopharmaceutical for PET Imaging of Myocardial Perfusion. PloS one 9, e109361, doi:10.1371/journal.pone.0109361 (2014).
37. Schonland, S. O. et al. Immunohistochemistry in the classification of systemic forms of amyloidosis: a systematic investigation of 117 patients. Blood 119, 488-493, doi:10.1182/blood-2011-06-358507 (2012).
38. Ward, J. E. et al. Doxycycline reduces fibril formation in a transgenic mouse model of AL amyloidosis. Blood 118, 6610-6617, doi:10.1182/blood-2011-04-351643 (2011).
39. Wall, J. S. et al. A novel method for quantifying peripheral tissue amyloid load by using the radiolabeled amyloidophilic peptide, p5. Amyloid 20, 21-26, doi:10.3109/13506129.2012.757216 (2013).
40. Babcock, J. J. & Brancaleon, L. Bovine serum albumin oligomers in the E-and B-forms at low protein concentration and ionic strength. Int. J.Biol. Macromol. 53, 42-53, doi:10.1016/j.ijbiomac.2012.10.030 (2013).
41. Bieschke, J. et al. Autocatalytic self-propagation of misfolded prion protein. Proc. Natl. Acad. Sci. U. S. A. 101, 12207-12211, doi:10.1073/pnas.0404650101 (2004).
42. Ehrnhoefer, D. E. et al. EGCG redirects amyloidogenic polypeptides into unstructured, off-pathway oligomers. Nat Struct Mol Biol 15, 558-566, doi:10.1038/nsmb.1437 (2008).
43. Cohen, E., Bieschke, J., Perciavalle, R. M., Kelly, J. W. & Dillin, A. Opposing activities protect against age-onset proteotoxicity. Science 313, 1604-1610, doi:10.1126/science.1124646 (2006).
44. Du, D. et al. A kinetic aggregation assay allowing selective and sensitive amyloid-beta quantification in cells and tissues. Biochemistry (Mosc). 50, 1607-1617, doi:10.1021/bi1013744 (2011).

What is claimed is:

1. A method of detecting light chain (LC) amyloid comprising:
   (i) receiving a biological sample from a subject;
   (ii) providing an imaging agent comprising a nanoparticle and anorganic heterocyclic molecule of the formula

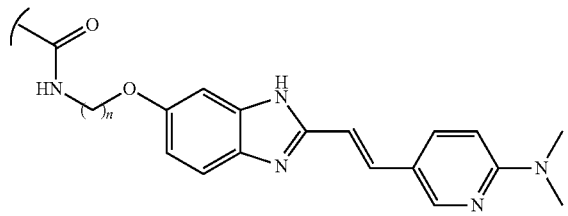

or a pharmaceutically acceptable salt, solvate or polymorph thereof, including all tautomers and stereoisomers thereof, wherein n=3 or 4,
wherein,

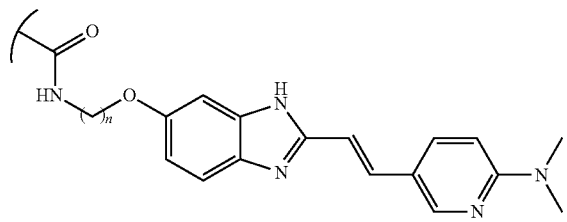

is a bond connecting the organic heterocyclic molecule to the rest of the imaging agent:

the imaging agent is capable of specific LC amyloid or LC aggregate binding having a Kd of about 600 pM or less;

(iii) contacting the nanoparticle to the biological sample or LC amyloid isolated or amplified from the biological sample; and (iv) detecting a binding value of the nanoparticle to an LC amyloid.

2. The method of claim 1 comprising amplifying the LC amyloid comprising:
  (A) performing or having performed isolating light chain (LC) aggregates from the biological sample, resulting in isolates; incubating the isolates in a fibrillation buffer; providing rare AL amyloid particles to seed the amplification; creating a seed by amyloid fragmentation; and catalyzing amyloid formation; or
  (B) performing or having performed providing a fixed amount of recombinantly expressed monomeric LC; adding the fixed amount of recombinantly expressed monomeric LC as a substrate to seed from the biological sample; and amplifying the monomeric LC, resulting in amyloid; and
  (ii) performing or having performed quantifying LC amyloid by determining lag time ($t_{lag}$) from the imaging agent fluorescence amplitude and comparing to a reference.

3. The method of claim 1, further comprising depleting albumin in the biological sample.

4. The method of claim 1, wherein the LC aggregates comprise rigid unbranched aggregates of fibrils and the fibrils consist of proteins arranged in anti-parallel, cross β-pleated sheet configuration comprising strands perpendicular to a filament long axis.

5. The method of claim 1, wherein the LC amyloid is detected in bone marrow, a kidney, a heart, a liver, a spleen, peripheral nerves, skin, a GI tract, serum, urine, urinary tract, tracheobronchial tree, conjunctiva, or thyroid.

6. The method of claim 1, wherein
κ and λ soluble free LC (sFLCs) concentrations are measured;
a higher concentration, compared to a standard or control, of soluble free light chains (sFLCs) in the biological sample indicates that the subject has amyloidosis or renal failure;
the subject is treated for multiple myeloma (MM) with amyloidosis if FLCs concentration is higher than a standard or control; or
the subject is treated for MM without amyloidosis if FLCs concentration is not higher than a standard or control.

7. The method of claim 1, further comprising stratifying the subject for AL MM therapeutic intervention or non-AL MM therapeutic intervention.

8. The method of claim 1, wherein the biological sample is selected from one or more of: urine, blood, serum, saliva, plasma, biopsy sample, bone marrow aspirate, cardiac tissue, organ sample, and tissue sample.

9. The method of claim 1, wherein the imaging agent further comprises a linker.

10. The method of claim 1, wherein the organic heterocyclic molecule has high affinity for amyloid-based aggregates comprising beta-sheet structures, wherein the high affinity corresponds to (i) a Kd value less than about 600 pM to LC amyloid or (ii) a Kd of at most about 600 pM to LC amyloid.

11. The method of claim 1, wherein the nanoparticle comprises Au, $^{199}$Au, $^{198}$Au, Cu, or $^{64}$Cu.

12. The method of claim 9, wherein the linker is a PEG or PEG derivative suitable for facilitating renal excretion and high-contrast imaging.

13. The method of claim 1, wherein the imaging agent is capable of detecting λ light chains or κ light chains;

is a PET imaging agent comprising a radiolabel;

is a fluorescence imaging agent;

is detected using a fluorescence microplate reader; or comprises a PET radionuclide into the nanoparticle.

14. The method of claim 1, wherein the imaging agent is capable of binding AL light chains when the imaging agent is present at sub-nanomolar concentrations.

15. The method of claim 1, wherein the imaging agent is water-soluble.

16. The method of claim 9, wherein the imaging agent comprises Cu-NP-194 or Au-NP-194, wherein the linker is PEG, and the nanoparticle comprises $^{64}$Cu, $^{199}$Au, or $^{198}$Au.

17. A method of detecting light chain (LC) amyloid comprising:

(i) receiving a biological sample from a subject;

(ii) providing an imaging agent comprising a nanoparticle and an organic heterocyclic molecule of the formula or a pharmaceutically acceptable salt, solvate or polymorph thereof, including all tautomers and stereoisomers thereof, wherein n=3 or 4, wherein, is a bond connecting the organic heterocyclic molecule to the rest of the imaging agent;

the imaging agent is capable of specific LC amyloid or LC aggregate binding having a Kd value of about 600 pM or less;

(iii) contacting the nanoparticle to the biological sample or LC amyloid isolated or amplified from the biological sample; and (iv) detecting a binding value of the nanoparticle to an LC amyloid, wherein the LC aggregates comprise rigid unbranched aggregates of fibrils and the fibrils consist of proteins arranged in anti-parallel, cross β-pleated sheet configuration comprising strands perpendicular to a filament long axis.

18. A method of detecting light chain (LC) amyloid comprising:

(i) receiving a biological sample from a subject;

(ii) providing an imaging agent comprising a nanoparticle and an inorganic heterocyclic molecule of the formula

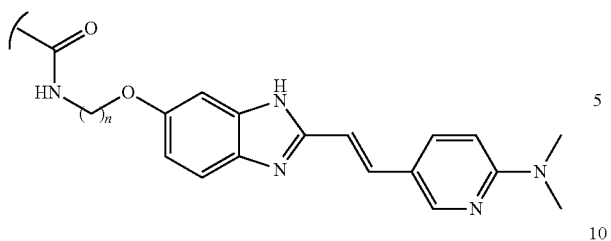

or a pharmaceutically acceptable salt, solvate or polymorph thereof, including all tautomers and stereoisomers thereof, wherein n=3 or 4, wherein, is a bond connecting the organic heterocyclic molecule to the rest of the imaging agent;

the imaging agent is capable of specific LC amyloid or LC aggregate binding having a Kd value of about 600 pM or less;

(iii) contacting the nanoparticle to the biological sample or LC amyloid isolated or amplified from the biological sample; and (iv) detecting a binding value of the nanoparticle to an LC amyloid, wherein the LC amyloid is detected in bone marrow, a kidney, a heart, a liver, a spleen, peripheral nerves, skin, a GI tract, serum, urine, urinary tract, tracheobronchial tree, conjunctiva, or thyroid.

* * * * *